United States Patent [19]
Pryor

[11] 4,394,284
[45] Jul. 19, 1983

[54] STABILIZED METHYLCHLOROFORM COMPOSITION

[75] Inventor: Alvetta Pryor, Houston, Tex.

[73] Assignee: The Dow Chemical Company, Midland, Mich.

[21] Appl. No.: 403,961

[22] Filed: Aug. 2, 1982

Related U.S. Application Data

[63] Continuation-in-part of Ser. No. 234,279, Feb. 3, 1981, abandoned, which is a continuation-in-part of Ser. No. 169,864, Jul. 17, 1980, abandoned.

[51] Int. Cl.$^3$ .................. C23G 7/52; C11D 5/02
[52] U.S. Cl. .................... 252/153; 252/162; 252/171; 252/172; 252/364; 252/DIG. 8; 252/DIG. 9; 134/31; 134/40; 134/42; 570/110; 570/115; 570/116
[58] Field of Search ............... 252/172, 171, 162, 153, 252/DIG. 8, DIG. 9, 364; 134/42, 40, 31; 570/110, 115, 116

[56] References Cited

U.S. PATENT DOCUMENTS

| | | | |
|---|---|---|---|
| 2,838,458 | 6/1958 | Bachtel | 252/171 |
| 2,970,113 | 1/1961 | Bachtel | 252/171 |
| 3,049,571 | 8/1962 | Brown | 260/652.5 |
| 3,060,125 | 10/1962 | Sims | 252/153 |
| 3,113,155 | 12/1963 | Sims | 260/652.5 |
| 3,281,480 | 10/1966 | Hardies | 252/172 |
| 3,467,722 | 9/1969 | Archer et al. | 252/172 |
| 3,518,202 | 6/1970 | McDonald | 252/171 |
| 3,549,715 | 12/1970 | Cormany et al. | 260/652.5 |
| 3,565,811 | 2/1971 | McDonald | 252/171 |
| 3,629,128 | 12/1971 | Rains | 252/171 |
| 3,676,355 | 7/1972 | Vuillemenot | 252/172 |
| 3,864,413 | 2/1975 | Beckers | 260/652.5 R |
| 3,959,397 | 5/1976 | Richtenzain et al. | 252/171 |
| 3,974,230 | 8/1976 | Archer et al. | 260/652.5 R |
| 4,115,461 | 9/1978 | Spencer et al. | 252/171 |
| 4,189,397 | 2/1980 | Allen | 252/171 |

FOREIGN PATENT DOCUMENTS

| 47-25107 | 10/1972 | Japan . |
| 48-00504 | 1/1973 | Japan . |
| 48-33514 | 10/1973 | Japan . |
| 49-109302 | 10/1974 | Japan . |
| 50-25509 | 3/1975 | Japan . |

*Primary Examiner*—H. S. Cockeram
*Attorney, Agent, or Firm*—Ac Ancona

[57] ABSTRACT

A nitroalkane-free inhibitor system for methylchloroform has been formulated which contains dioxane, an alkylene oxide, and 3-butyn-1-ol. The stabilizer amounts to about 4 to 6% by volume of the stabilized methylchloroform composition. The stabilized composition is useful in vapor degreasing applications when it additionally contains an alkyl nitrate.

3 Claims, No Drawings

STABILIZED METHYLCHLOROFORM COMPOSITION

CROSS-REFERENCE TO RELATED APPLICATION

This application is a continuation-in-part of my copending application Ser. No. 234,279, filed Feb. 13, 1981 which is a continuation-in-part of application Ser. No. 169,564, filed July 17, 1980, both now abandoned.

BACKGROUND OF THE INVENTION

Methylchloroform is subject to degradation and forms corrosive products in the presence of certain metals, especially aluminum, zinc, iron, copper and their alloys. Most stabilized methylchloroform compositions contain a combination of compounds as the stabilizer, some of which are intended to stabilize either the vapor or liquid and others which will be effective in both. The particular ones required will depend upon the use for which the methylchloroform is intended. This solvent is useful in cold cleaning, hot cleaning and in vapor degreasing. Since the introduction into the marketplace in 1957-1958 as a commodity the largest volume of 1,1,1-trichloroethane sold throughout the world contained 1,4-dioxane, nitromethane and 1,2-butylene oxide as the sole inhibitors. The next largest volume has been that containing 1,3-dioxolane (a five-membered dioxygen heterocycle, a compound very similar to 1,4-dioxane), nitromethane, 1,2-butylene oxide and in most instances one or more materials (such as lower ketones and/or alcohols) which account for the remainder of the ten principal compounds used in industry to stabilize 1,1,1-trichloroethane. To illustrate the wide variety of stabilizers used in combination with the nitroalkanes, numerous patents may be cited. In U.S. Pat. No. 2,970,113 an acetylenic alcohol and dioxane are employed with nitroalkanes; U.S. Pat. No. 3,049,571 employs sec-butyl alcohol, an alkynol, dioxane and butylene oxide in addition to the nitroalkanes. U.S. Pat. Nos. 3,518,202 and 3,549,715 both employ acetylenic alcohols along with nitroalkanes and auxilliary stabilizer components. Other patents employ esters (U.S. Pat. No. 3,060,125); esters and dioxane (U.S. Pat. No. 3,113,155); tert-butyl alcohol, butylene oxide and ethers (U.S. Pat. No. 3,281,480); and amines, butylene oxide and dioxane (U.S. Pat. No. 3,629,128). Even more recently issued patents employ dioxane, t-amyl alcohol and butylene oxide in combination with a nitroalkane (U.S. Pat. No. 4,115,461) and the combination of glycidol, dioxane and butylene oxide (U.S. Pat. No. 4,152,359).

U.S. Pat. No. 3,974,230 employs either a mixture of methyl butynol and t-amyl alcohol or methyl butynol alone or along with nitroalkanes and alkylene oxides as the stabilizing component.

In the light of recent attacks by environmentalists on some of the chlorinated hydrocarbons, allegedly due to their environmental hazards, as well as controls concerning their use resulting from the Occupational Safety and Health Act, it becomes necessary for the manufacturers of 1,1,1-trichloroethane to provide this safer solvent, from an environmental, safety and health standpoint, with inhibitor systems which will be in comformance with environmental standards.

It is the object of the present invention to provide an industrially useful combination of stabilizers for 1,1,1-trichloroethane which will inhibit, even under the severe stress of vapor degreasing, the 1,1,1-trichloroethane-aluminum reaction as well as the reactions attributable to the presence of zinc, copper and iron, their alloys, and water.

The inhibitors employed to stabilize methyl chloroform against aluminum and zinc, i.e. dioxane and butylene oxide are not very effective for any appreciable length of time in the absence of a nitroalkane.

The present invention employs a stabilizer for methylchloroform in which the nitroalkane is replaced with an alkynol. In this stabilizer combination no nitroalkane is required.

BRIEF DESCRIPTION OF THE INVENTION

In the present stabilizer composition, 3-butyn-1-ol is employed in combination with dioxane, butylene oxide and for vapor degreasing additionally an alkyl nitrate as the stabilizer for methylchloroform. The thus-stabilized solvent requires no nitroalkane and is useful in the presence of aluminum metal.

DETAILED DESCRIPTION OF THE INVENTION

Various compounds were tested as a replacement for nitromethane in formulations employed to stabilize 1,1,1-trichloroethane. Although a number of acetylenic alcohols were tested, only 3-butyn-1-ol was effective.

Test Procedure A

The concentration of 3-butyn-1-ol was established at 0.5 vol. percent and all other stabilizers were varied. Four hundred thirty g. of the inhibited methylchloroform solution was placed in a one-liter flask equipped with a condensate reservoir with a reflux condenser. The solution was refluxed at approximately 80° C. and the fraction was collected until it began to return for reboiling. Both top and bottom fractions were used in the seven-day reflux test.

The procedure for a seven-day reflux test was as follows: Ten ml. of the new inhibitor system as formulated was placed in a test tube and a metal coupon or approximately 0.5 g. of metal fragments were placed in the solvent. The depth of the liquid was such that one half of the coupon was exposed to the liquid and the other half to the vapor. A boiling stone was added and the tubes closed with a glass stopper. The samples were refluxed in a heating block for seven days at approximately 80° C. or until terminated, due to corrosion of the metal or discoloration of the solutions. The extent of corrosion was rated by visual observation of both metal and solution on a scale from 0 to 5, the lower the number, the less the corrosion. A zero rating indicates seven days of refluxing without visible signs of corrosion on the metal or in the solution. A number in parenthesis indicates the number of days without corrosion. The metals used in this test were Al-2024 coupons and chips, mossy zinc and zinc coupons, brass coupons, copper wire and steel rod. They were tested either singly or in combination.

Table I shows the compositions of the inhibitors which were found most effective.

TABLE I

| Example No. | Stabilizer Components (V/V %) | | | |
|---|---|---|---|---|
| | Dioxane | B.O. | Butynol | RONO$_2$ |
| 1 | 3.0 | 0.75 | 0.5 | n-Pr 1.0 |
| 2 | 3.0 | 0.75 | 0.5 | i-Pr 1.0 |
| 3 | 3.0 | 0.75 | 0.5 | i-Pr 0.75 |
| 4 | 2.5 | 0.75 | 0.5 | i-Pr 1.5 |

TABLE I-continued

| Example No. | Stabilizer Components (V/V %) | | | |
|---|---|---|---|---|
| | Dioxane | B.O. | Butynol | RONO$_2$ |
| 5 | 3.0 | 0.75 | 0.5 | Et 1.0 |
| 6 | 3.0 | — | 0.5 | i-Pr 1.0 |
| 7 | 2.0 | 0.75 | 0.5 | Et 1.5 |
| 8 | 4.0 | 2.0 | 0.4 | — |
| 9 | 2.0 | 2.0 | 0.4 | — |
| 10 | 1.95 | 1.95 | 0.1 | — |
| 11 | 1.9 | 1.9 | 0.2 | — |
| 12 | 1.65 | 1.65 | 0.7 | — |
| 13 | 1.55 | 1.55 | 0.9 | — |
| 14 | 1.5 | 1.5 | 1.0 | — |

Table II shows the ratings, as defined previously, of the above stabilizer compositions (Table I) in the 7-day reflux test.

TABLE II

| Example No. | Metals | | | | | |
|---|---|---|---|---|---|---|
| | Al coup | Al chips | Zn coup | Zn mossy | Al & Zn coup | Al chips & Zn mossy |
| 1 | 1 | 1 | 0 | 0 | 0 | 0 |
| 2 | 0 | (3) | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| 6 | 0 | 0 | 0 | 0 | 0 | 0 |
| 7 | 0 | 0 | 0 | 0 | 0 | 0 |
| 8 | 0 | 0 | 0 | 0 | 0 | 0 |
| 9 | 0 | 0 | 0 | 0 | 0 | 0 |
| 10* | 2 | — | — | — | — | — |
| 11* | 0 | — | — | — | — | — |
| 12* | 0 | — | — | — | — | — |
| 13* | 0 | — | — | — | — | — |
| 14* | 0 | — | — | — | — | — |

*Examples 10–14 were tested with the aluminum coupons only.

Thus, the formulations which are effective are within the ranges containing 1.5-4% dioxane, 0.75 to 2% butylene oxide and 0.1-1% 3-butyn-1-ol, all percentages being by volume and based on the total volume of stabilizers and 1,1,1-trichloroethane. Optionally the stabilizer formulation may contain 0.75 to 1.5 vol. % of ethyl or propyl nitrates, or mixtures thereof.

Some of the formulations, the ratings of which were given in Table II were further evaluated by employing the environmental conditions of a vapor degreaser were simulated in the laboratory. The apparatus was constructed from a glass 300 ml. and 500 ml. round bottom flask which were fused at the sides by a connector to allow the exchange of vapors in each chamber. Total capacity of the smaller chamber (dip) and larger (sump) was approximately 240 ml. and 260 ml., respectively.

Five hundred ml. of the solvent was placed in the degreaser via the dip chamber. The solution was refluxed one to two days to allow distribution of the inhibitors among the chambers. The dip was maintained between 65° C. and 70° C., and the sump refluxed between 75° C. and 78° C. Aliquots of the solutions were withdrawn periodically and analyzed by gas chromatography. On the second day, 13.5 ml. of Exxon Isopar L was added to the sump and the refluxing continued for an additional two days. Inhibitor distribution was rechecked, metal fragments added to each chamber; and the refluxing continued for seven days with periodic analyses of each solution. Solvent adjustments were made after every second analyses. The chambers contained the following metal fragments:

| 1.42 g | Al 2024 chips |
|---|---|
| 0.46 g | steel wool |
| 3.5 g | 70/30 brass chips |
| 2.1 g | mossy zinc pellets (dip) |
| 3.5 g | mossy zinc pellets (sump) |

After terminating the simulation test, each solution was withdrawn from the chambers and was tested further by the seven-day reflux test. In addition to the metals listed in the 7-day reflux test, steel wool was substituted for 1018-steel rod and iron filings included in the test.

When fractionated certain of the above compositions failed to inhibit in either the top (dip) or bottom (sump) fraction due to one or more of the inhibitors being lost from the bottom fraction or failing to go overhead with the solvent. Thus, the data in Table III shows seven-day reflux results on top and bottom fractions of certain of the above compositions. The ratings indicate the poorest evaluation on any one or more of the metals tested.

TABLE III

| Example No. | Top | Bottom |
|---|---|---|
| 2 | 3 | 0 |
| 5 | 4 | 0 |
| 6 | 4 | 4 |
| 7 | 0 | 0 |
| 8 | 4 | 4 |
| 9 | 5 | 0 |

The unfractionated materials (Table II) would be satisfactory for any use which did not result in a separation of one or more of the inhibitors, as in a vapor degreaser. The only composition which can be used successfully in a vapor degreaser is that of Example 7, while Example 2 is borderline, in which aluminum chips gave a rating greater than 0, while the remaining metals gave essentially no corrosion, i.e. a rating of 0. (These contain 2.0–3.0% dioxane, 0.75% B.O., 0.5% butynol and 1.5% ethyl or iso-propyl nitrates.)

What is claimed is:

1. A stabilizer composition for 1,1,1-trichloroethane wherein the stabilizer consists essentially of 1.5 to 4 vol. % dioxane, 0.75 to 2 vol. % butylene oxide and 0.1 to 1.0 vol. % 3-butyn-1-ol based on the total volume of stabilizer and trichloroethane.

2. The composition of claim 1 suitable as a vapor degreasing solvent which additionally contains 0.75 to 1.5 vol. % of an alkyl nitrate having 2–3 carbon atoms.

3. A stabilized 1,1,1-trichloroethane solvent employed in a vapor degreasing process which consists essentially of 2.0 to 3.0% dioxane, 0.75% butylene oxide, 0.5% 3-butyn-1-ol, 1.5% of ethyl or isopropyl nitrate and the remainder trichloroethane all based on the total volume of solvent plus inhibitors.

* * * * *